(12) United States Patent
Hickingbotham

(10) Patent No.: US 8,012,146 B2
(45) Date of Patent: Sep. 6, 2011

(54) EXTENDING SMALL-GAUGE ILLUMINATOR

(75) Inventor: Dyson Hickingbotham, Stouchberg-Womelsdorf, PA (US)

(73) Assignee: Novartis AG, Basel (CH)

( * ) Notice: Subject to any disclaimer, the term of this patent is extended or adjusted under 35 U.S.C. 154(b) by 715 days.

(21) Appl. No.: 11/590,392

(22) Filed: Oct. 31, 2006

(65) Prior Publication Data

US 2007/0255264 A1 Nov. 1, 2007

Related U.S. Application Data

(60) Provisional application No. 60/731,843, filed on Oct. 31, 2005.

(51) Int. Cl.
*A61B 18/18* (2006.01)

(52) U.S. Cl. ............... 606/15; 606/16; 606/4; 362/577

(58) Field of Classification Search .......... 606/4–16; 362/804, 572–275, 577; 600/249, 236
See application file for complete search history.

(56) References Cited

U.S. PATENT DOCUMENTS

| 4,870,952 | A | * | 10/1989 | Martinez ...................... 362/572 |
| 5,855,577 | A | * | 1/1999 | Murphy-Chutorian et al. .. 606/7 |
| 6,572,608 | B1 | * | 6/2003 | Lee et al. ........................ 606/15 |
| 2003/0171722 | A1 | | 9/2003 | Paques et al. | |
| 2004/0215065 | A1 | | 10/2004 | Setten | |
| 2005/0075628 | A1 | | 4/2005 | Cazzini et al. | |
| 2006/0184162 | A1 | * | 8/2006 | Smith ............................. 606/4 |
| 2007/0100327 | A1 | * | 5/2007 | Smith ............................. 606/4 |

FOREIGN PATENT DOCUMENTS

| EP | 1522290 A1 | 4/2005 |
| RU | 2209054 | 7/2003 |
| WO | WO 9722304 A1 | 6/1997 |
| WO | WO 0119255 A1 | 3/2001 |
| WO | WO 2005/070490 | 8/2005 |

OTHER PUBLICATIONS

International Search Report for PCT/US2006/042397, Publication No. WO2007/053590, 5 pages.
PCT International Preliminary Report on Patentability, PCT/US2006/042397, Oct. 31, 2006, 5 pages.

* cited by examiner

*Primary Examiner* — Eduardo C Robert
*Assistant Examiner* — Christina Negrelli
(74) *Attorney, Agent, or Firm* — Darien L. Reddick

(57) ABSTRACT

A variable-rigidity, small-gauge illuminator is disclosed, one embodiment being a small-gauge illumination surgical system comprising: a light source for providing a light beam; an optical cable, optically coupled to the light source for receiving and transmitting the light beam; a handpiece, operably coupled to the optical cable; an optical fiber, operably coupled to the handpiece, wherein the optical fiber is optically coupled to the optical cable to receive and transmit the light beam to illuminate an area; and a cannula, operably coupled to the handpiece, for housing and directing the optical fiber, wherein the cannula is operable to extend and retract from the handpiece to vary the length of the cannula extending from the handpiece, and wherein the optical fiber is operably connected to the cannula.

35 Claims, 5 Drawing Sheets

EXTENDING SMALL-GAUGE ILLUMINATOR

CROSS-REFERENCE TO RELATED APPLICATIONS

This application claims priority under 35 U.S.C. §119 to U.S. Provisional Patent Application No. 60/731,843, filed Oct. 31, 2005, the entire contents of which are incorporated herein by reference.

TECHNICAL FIELD OF THE INVENTION

The present invention relates generally to surgical instrumentation. In particular, the present invention relates to surgical instruments for illuminating and manipulating an area during eye surgery. Even more particularly, the present invention relates to an extending, variable rigidity, small-gauge wide-angle illuminator for illumination of a surgical field.

BACKGROUND OF THE INVENTION

In ophthalmic surgery, and in particular in vitreo-retinal surgery, it is desirable to use a wide-angle surgical microscope system to view as large a portion of the retina as possible. Wide-angle objective lenses for such microscopic systems exist, but they require a wider illumination field than that provided by the cone of illumination of a typical fiber-optic probe. As a result, various technologies have been developed to increase the beam spreading of the relatively incoherent light provided by a fiber-optic illuminator. These known wide-angle illuminators can thus illuminate a larger portion of the retina as required by current wide-angle surgical microscope systems. Currently existing wide-angle illuminators, however, display several disadvantages.

One disadvantage of prior art small gauge, wide-angle illuminators for ophthalmic surgery is the lack of rigidity of the cannula that is inserted into and extends into the eye. In ophthalmic surgery, such as vitreo-retinal surgery, the primary function of an illumination probe is to provide illumination for the surgical area. A secondary function is to manipulate portions of the eye near the surgical area to provide an unobstructed view and to allow access to a surgical area, such as the periphery of the retina. However, to manipulate tissue within the eye, the illuminator cannula must have a certain rigidity. Due to their larger diameter, the cannulas of 20 gauge devices provide adequate rigidity for surgeons to manipulate tissue in the eye. However, 25 gauge devices have a smaller diameter cannula (e.g., 0.0205 inches) with thin walls resulting in a much more flexible probe (cannula) than a same length 20 gauge cannula. Prior art small-gauge illuminaters (<20 gauge) do not, therefore, provide sufficient rigidity to effectively manipulate tissue in the eye in the manner of larger gauge illuminators.

Therefore, a need exists for a small-gauge wide-angle illuminator for illumination of a surgical field that can reduce or eliminate the problem of lack of rigidity for manipulating eye tissue associated with prior art small gauge, wide-angle illuminators.

BRIEF SUMMARY OF THE INVENTION

The embodiments of the extending, variable-rigidity, small-gauge illuminator for illumination of a surgical field of the present invention substantially meet this need and others. One embodiment of the variable-rigidity illuminator of this invention is a small-gauge, wide-angle illumination surgical system comprising: a light source for providing a light beam; an optical cable, optically coupled to the light source for receiving and transmitting the light beam; a handpiece, operably coupled to the optical cable; an optical fiber, operably coupled to the handpiece, wherein the optical fiber is optically coupled to the optical cable to receive and transmit the light beam to illuminate an area; and a cannula, operably coupled to the handpiece, for housing and directing the optical fiber, wherein the cannula is operable to extend and retract from the handpiece to vary the length of the cannula extending from the handpiece, and wherein the optical fiber is operably connected to the cannula such that the distal end of the optical fiber and the distal end of the cannula remain co-incident as the length of the cannula extending from the handpiece is varied.

Embodiments of the present invention can further comprise an optical element, optically coupled to a distal end of the optical fiber, for receiving the light beam and scattering the light beam to illuminate the area (e.g., a surgical site). The optical element can be a small-gauge, diffusive optical element as known to those having skill in the art. Further, the optical element, the cannula and the handpiece can be fabricated from biocompatible materials and can be 23 or 25 gauge, or other small-gauge as known to those familiar with the art. The optical cable can comprise a first optical connector operably coupled to the light source and a second optical connector operably coupled to the handpiece (to optically couple the optical cable to the optical fiber housed within the handpiece and cannula). These connectors can be SMA optical fiber connectors. The optical element, optical fiber and optical cable (i.e., the optical fiber(s) within the optical cable) should be of a compatible gauge so as to transmit the light beam from the light source to the surgical field. For example, all three elements could be of equal gauge.

To enable some of the advantages of the embodiments of this invention, the cannula and optical fiber can be operably coupled to the handpiece to enable linear displacement of the cannula and optical fiber within the handpiece. The handpiece can include a means, such as a push/pull mechanism, for adjusting the linear displacement of the cannula and optical fiber. For example, the cannula can be operably mounted onto a piston controlled by a knob that an operator can slide to extend or retract the cannula and optical fiber from or into the handpiece. Other adjusting means as known to those having skill in the art can also be used.

Other embodiments of the present invention can include a method for illumination of a surgical field using a variable-rigidity, small-gauge illuminator in accordance with the teachings of this invention, and a surgical handpiece embodiment of the variable-rigidity, small-gauge illuminator of the present invention for use in ophthalmic surgery. Embodiments of this invention can be implemented as a handpiece or other housing connected to an extendable cannula including an optical fiber in accordance with the teachings of this invention. Further, embodiments of this invention can be incorporated within a surgical machine or system for use in ophthalmic or other surgery. Other uses for a variable-rigidity, small-gauge illuminator designed in accordance with the teachings of this invention will be known to those having ordinary skill in the art.

BRIEF DESCRIPTION OF THE SEVERAL VIEWS OF THE DRAWINGS

A more complete understanding of the present invention and the advantages thereof may be acquired by referring to the following description, taken in conjunction with the accompanying drawings, in which like reference numbers indicate like features and wherein.

DETAILED DESCRIPTION OF THE INVENTION

Figure 1:
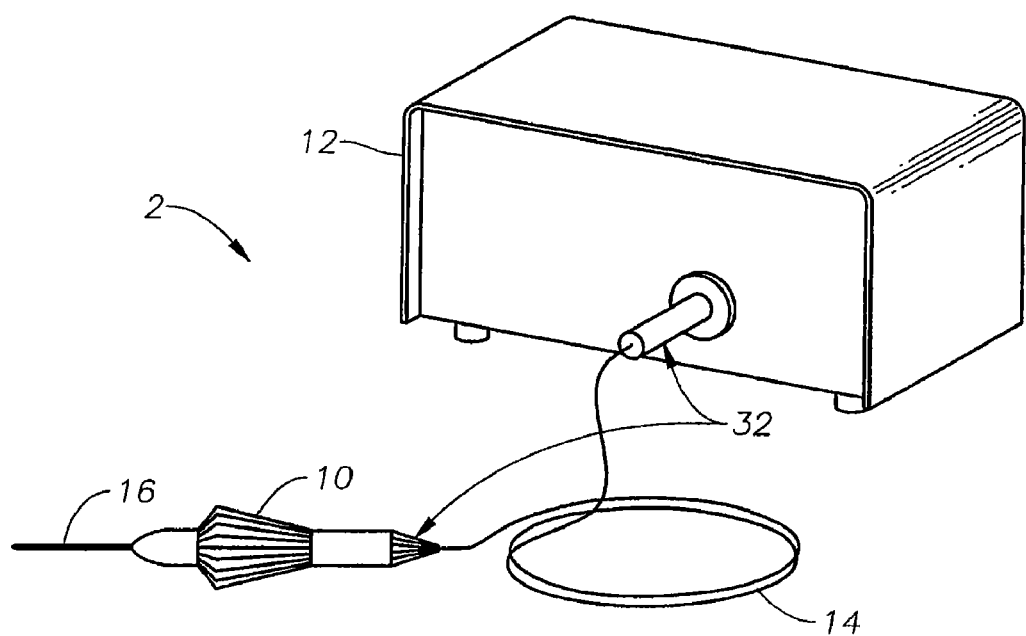
FIG. 1 is a diagrammatic representation of one embodiment of a system for illumination and tissue manipulation in accordance with the teachings of this invention.

Preferred embodiments of the present invention are illustrated in the FIGURES, like numerals being used to refer to like and corresponding parts of the various drawings.

The various embodiments of the present invention provide for a small gauge (e.g., 23 or 25 gauge) optical fiber based endo-illuminator device for use in surgical Jo procedures, such as in vitreo-retinal/posterior segment surgery. Embodiments of this invention can comprise a handpiece, such as the Alcon-Grieshaber Revolution-DSP$^{Th}$ handpiece sold by Alcon Laboratories, Inc., Fort Worth, Tex., connected to a small gauge cannula (e.g., 23 or 25 gauge). The inner dimension of the cannula can be used to house an optical fiber, which can terminate in a diffusive optical element, in accordance with the teachings of this invention. Embodiments of the variable-rigidity illuminator can comprise a wide-angle illuminator and all embodiments can be configured for use in the general field of ophthalmic surgery. However, it is contemplated and it will be realized by those skilled in the art that the scope of the present invention is not limited to ophthalmology, but may be applied generally to other areas of surgery where wide-angle and/or variable illumination involving tissue manipulation may be required.

The embodiments of the present invention provide an operator the ability to extend the cannula of the illuminator between a maximum extended length and a minimum extended length, which can be arbitrarily set. The operator can vary the length of the cannula and optical fiber extending from the illuminator handpiece by means of a knob or slide operably coupled to an extending means that is in turn operably coupled to the cannula/optical fiber. The knob or slide can be integral to the extending means and the extending means can comprise a piston, ratcheting mechanism, a slide or any other such means as will be known to those having skill in the art.

In the various embodiments of this invention, as the cannula length is shortened (cannula retracted into the handpiece), the cannula's effective stiffness is increased due to the shorter exposed length and vice-versa. Because the rigidity of the cannula is a function of the exposed cannula length and varies as a function of the exposed cannula length raised to the $3^{rd}$ power, minimizing the length of the cannula exposed from the handpiece has a significant impact on the rigidity of the cannula, and hence its usefulness in manipulating tissues within the eye. The variable-length cannula of the embodiments of the present invention provide a user the ability to use the full length of the cannula for certain applications requiring extending the illuminator tip (and hence the illumination) into the farther reaches of the eye, while also allowing a user to retract the cannula and shorten its length when increased rigidity is needed to manipulate tissue in the eye.

An embodiment of the variable-rigidity illuminator of this invention can comprise an optical fiber, cannula and handpiece fabricated from biocompatible polymeric materials, such that the invasive portion of the wide-angle illuminator is a disposable surgical item. Unlike the prior art, each embodiment of the variable-rigidity, small-gauge illuminator of this invention can provide high rigidity when needed to manipulate tissues, while still providing the extension needed to illuminate is the farther reaches of the eye. Embodiments of this invention fabricated from biocompatible polymeric materials can be integrated into a low cost, articulated handpiece mechanism, such that these embodiments can comprise an inexpensive disposable illuminator instrument.

FIG. 1 is a diagrammatic representation of a handpiece 10 for delivering a beam of incoherent light from a light source 12 through cable 14 to a stem 16. Cable 14 can be any gauge fiber optic cable as known in the art, but is preferably a cable having 23 or 25 gauge fiber. Further, cable 14 can comprise a single optical fiber or a plurality of optical fibers optically coupled to receive and transmit light from light source 12 to an optical fiber 22 within, and operably coupled to, stem (cannula) 16 through handpiece 10. Stem 16 is configured to house the optical fiber 22 and, in some embodiments, a diffusive optical element 20 at the distal end of stem 16. Stem 16 and optical fiber 22 are operable to vary in length (extending from handpiece 10) in response to operator input, as will be described more fully below. Coupling system 32 can comprise an optical fiber connector at each end of cable 14 to optically couple light source 12 to an optical fiber within handpiece 10, as discussed more fully below.

Figure 2:
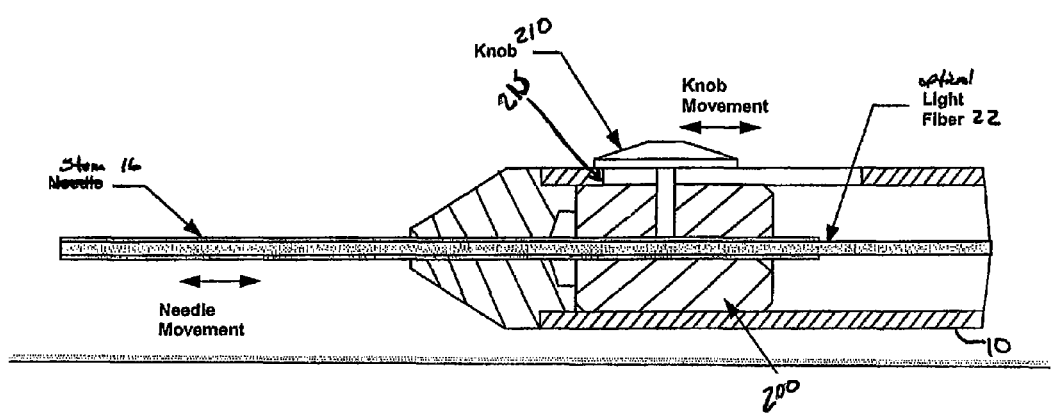
FIG. 2 is a more detailed diagram illustrating one embodiment of a variable-rigidity, small-gauge illuminator in accordance with the teachings of this invention.

FIG. 2 is a more detailed diagram illustrating one embodiment of a variable-rigidity, small-gauge illuminator of the present invention. Stem 16 is operably coupled to a piston 200 that is operably coupled to and controlled by a knob 210 or similar mechanisim. An operator can slide knob 210 toward the stem 16 tip (distal end) until the knob 210 hits a stop 215 and the stem 16 is fully extended. The knob 210 can also be slid backward toward the proximal end of the handpiece 10 until it hits a proximal stop (not shown) and the stem 16 is fully retracted. The piston 200/stem 16/knob 210 assembly can also comprise ratcheted points or friction points so that stem 16 can be positioned and maintained at selected points between full extension and full retraction without unintentional movement. Optical fiber 22 is positioned inside stem 16 and operably coupled to stem 16 such that the distal ends of stem 16 and optical fiber 22 remain coincident as stem 16 is retracted or extended.

The embodiments of the present invention provide advantages over the prior to art in that the mechanical extension and/or retraction they provide can be accomplished internal to the illuminator (e.g., handpiece 10), rather than having a surgeon manually compensate for the cannula (stem 16) length. This is particularly useful in that surgeons typically require the full length of the cannula only for short periods during the surgery. The embodiments of the present invention allow the surgeon to set the optimal cannula length throughout a surgical procedure.

FIG. 2 shows Stem 16 housing optical fiber 22, which can be optically coupled to fiber optic cable 14. In some embodiments, fiber optic cable 14 comprises an optical fiber that can extend through the handpiece 10 and is coupled directly to stem 16. For these embodiments, a separate fiber 22 is not used. When implemented within handpiece 10, fiber 22 is of a gauge compatible with the gauge of fiber optic cable 14 such that it can receive and transmit light from fiber optic cable 14. Handpiece 10 can be any surgical handpiece as known in the art, such as the Revolution-DSP™ handpiece sold by Alcon Laboratories, Inc. of Fort Worth, Tex. Light source 12 can be a xenon light source, a halogen light source, or any other light source capable of delivering light through a fiber optic cable. Stem 16 can be a small gauge cannula, preferably within the range of 23 to 30 gauge, as known to those having skill in the art. Stem 16 can be stainless steel or a suitable biocompatible polymer (e.g., PEEK, polyimide, etc.) as known to those having skill in the art.

The fiber optic cable 14 or fiber 22 housed within the stem 16 can be operably coupled to the stem 16, and stem 16 coupled to the handpiece 10, for example, via an adjusting means 210, as shown in FIG. 2. Adjusting means 210 can comprise for example, a simple push/pull mechanism as known to those having skill in the art. Light source 12 can be optically coupled to handpiece 10 (i.e., to fiber 22) using, for example, standard SMA (Scale Manufacturers Association) optical fiber connectors at the ends of fiber optic cable 14. This allows for the efficient coupling of light from the light source 12 through fiber optic cable 14 to the handpiece 10 and finally emanating from optical fiber 22, or alternatively, an optical element 20, at the distal end of the stem 16. Light source 12 may comprise filters, as known to those skilled in the art, to reduce the damaging thermal effects of absorbed infrared radiation originating at the light source. The light source 12 filter(s) can be used to selectively illuminate a surgical field with different colors of light, such as to excite a surgical dye.

Fiber(s) 22 (and/or 14, depending on the embodiment) can be terminated coincident with the distal end of stem 16. Activation of the adjusting means 210, by, for example, a gentle and reversible sliding action, can cause stem 16 to extend from (or retract into) the distal end of handpiece 10 by an amount determined and adjusted by sliding adjusting means 210/piston 200. The length and rigidity of stem 16 may thus be varied. In this way, a surgeon can adjust the rigidity of stem 16 as needed to manipulate and illuminate tissues within the eye. The adjusting means 210 of handpiece 10 can be any adjusting means as known to those having skill in the art.

In one embodiment of the variable-intensity, wide-angle illuminator of the present invention, a simple mechanical locking mechanism (e.g., friction or ratcheting mechanism), as known to those skilled in the art, can permit the length of stem 16 to be fixed, until released and/or re-adjusted by the user via the adjusting means 210.

Figure 3:
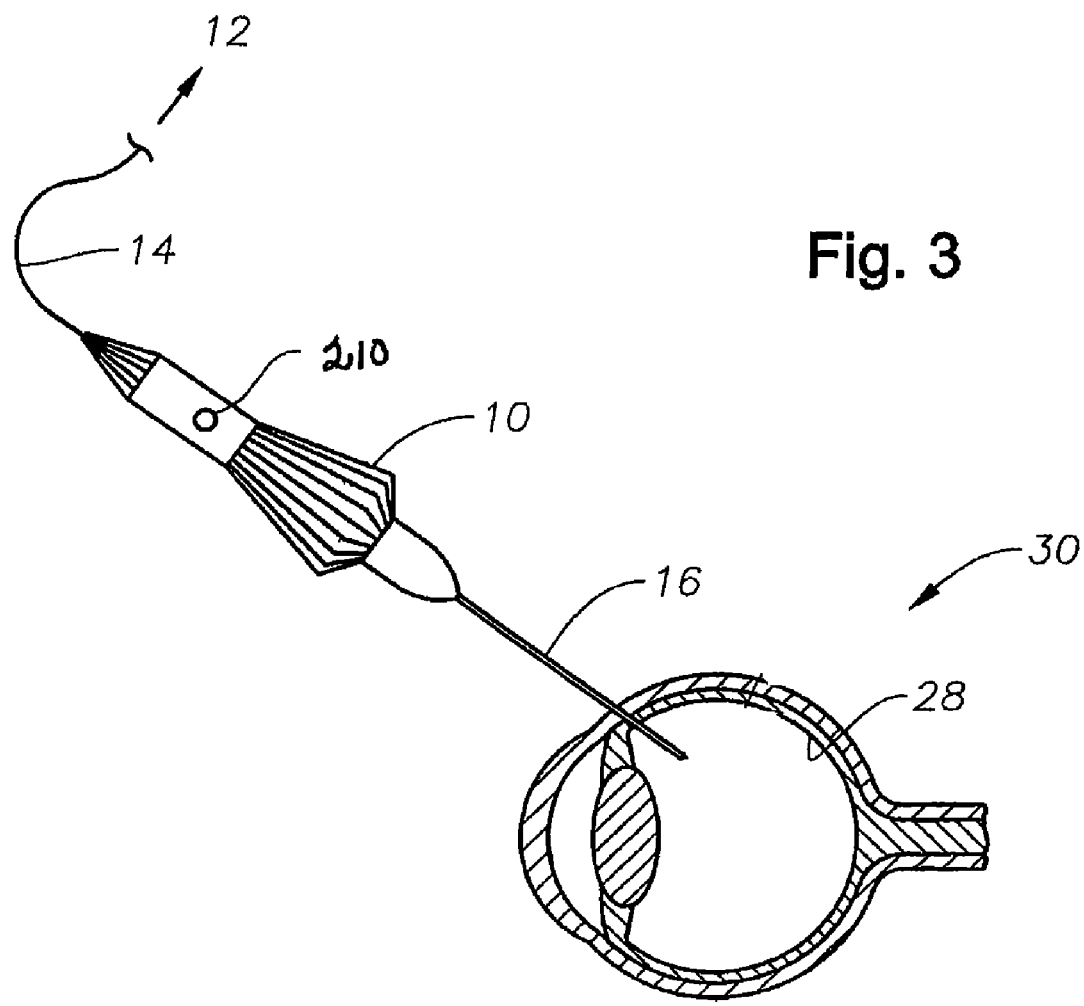
FIG. 3 is a diagram illustrating the use of an embodiment of an illuminator of the present invention for ophthalmic surgery.

FIG. 3 illustrates the use of one embodiment of the variable-rigidity, small-gauge illuminator of this invention in an ophthalmic surgery. In operation, handpiece 10 delivers a beam of light (e.g., a beam of spatially and temporally incoherent light having a broad spectral bandwidth) through stem 16 via optical fiber 22 to illuminate a retina 28 of an eye 30. The collimated light delivered through handpiece 10 (optical fiber 22/14) is generated by light source 12 and delivered to illuminate the retina 28 by means of fiber optic cable 14 and coupling system 32. Optical fiber 22, or, alternatively, an optical element optically coupled to the distal end of optical fiber 22, spreads the light beam delivered from light source 12 over as large an area of the surgical field as, for example, a microscopic wide-angle objective lens permits a surgeon to see. Stem 16's length and rigidity can be varied by a surgeon via adjusting means 210 as desired to manipulate tissue effectively within the eye.

Figure 4:
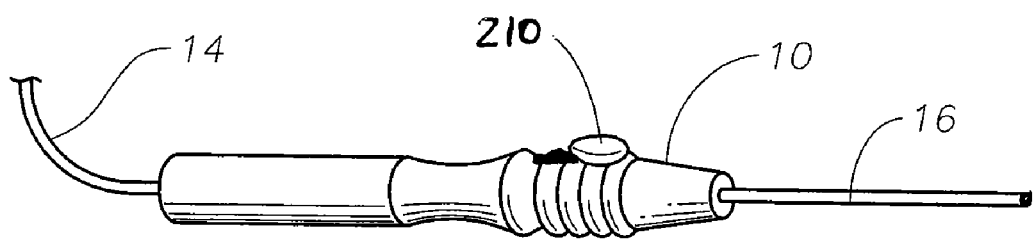
FIGS. 4 and 5 are diagrams illustrating an embodiment of the illuminator of the present invention in fully extended and fully retracted positions.
Figure 5:
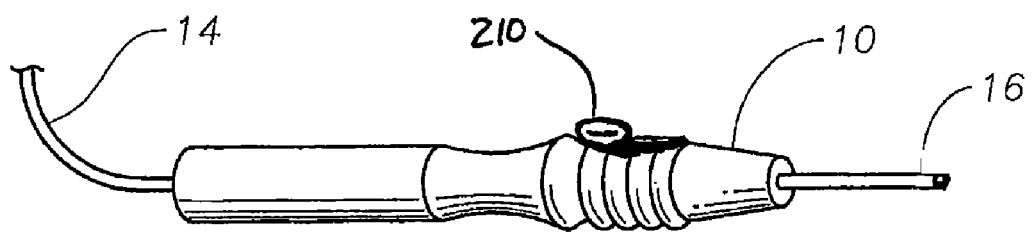

FIGS. 4 and 5 show an embodiment of the illuminator of the present invention with stem 16 in the fully extended position (FIG. 4) and the fully retracted position (FIG. 5). A surgeon can position stem 16 at any length between the maximum and minimum lengths, which can be arbitrarily set.

Although the present invention has been described in detail herein with reference to the illustrated embodiments, it should be understood that the description is by way of example only and is not to be construed in a limiting sense. It is to be further understood, therefore, that numerous changes in the details of the embodiments of this invention and additional embodiments of this invention will be apparent to, and may be made by, persons of ordinary skill in the art having reference to this description. It is contemplated that all such changes and additional embodiments are within the spirit and true scope of this invention as claimed below. Thus, while the present invention has been described in particular reference to the general area of ophthalmic surgery, the teachings contained herein apply equally wherever it is desirous to provide wide-angle illumination via a small-gauge incision and wherein tissue manipulation may be required.

What is claimed is:

1. An extendable wide-angle illumination surgical system comprising:
   a light source for providing a light beam;
   an optical cable, optically coupled to the light source for receiving and transmitting the light beam;
   a handpiece, operably coupled to the optical cable;
   an optical fiber, operably coupled to the handpiece, wherein the optical fiber is optically coupled to the optical cable to receive and transmit the light beam to illuminate an area;
   a cannula operably coupled to the handpiece, for housing and directing the optical fiber, wherein the cannula is operable to extend and tract from the handpiece to vary a length of the cannula extending from the handpiece;
   wherein the optical fiber is operably coupled to the cannula such that a distal end of the optical fiber and a distal end of the cannula remain co-incident as the length of the cannula extending from the handpiece is varied.

2. The extendable wide-angle illumination surgical system of claim 1, further comprising an optical element, optically coupled to a distal end of the optical fiber, for receiving the light beam and scattering the light beam to illuminate the area.

3. The extendable wide-angle illumination surgical system of claim 2, wherein the optical element comprises a small-gauge diffusive optical element.

4. The extendable wide-angle illumination surgical system of claim 3, wherein the optical element is operably coupled to the cannula such that a distal end of the optical element and a distal end of the cannula remain co-incident as the length of the cannula extending from the handpiece is varied.

5. The extendable wide-angle illumination surgical system of claim 1, wherein the optical fiber is a 19, 20 or 25 gauge optical fiber.

6. The extendable wide-angle illumination surgical system of claim 1, wherein the cannula, optical fiber and the handpiece are fabricated from biocompatible materials.

7. The extendable wide-angle illumination surgical system of claim 1, wherein the optical fiber is an integral part of the optical cable.

8. The extendable wide-angle illumination surgical system of claim 1, wherein the optical cable comprises a first optical connector operably coupled to the light source and a second optical connector operably coupled to the handpiece.

9. The extendable wide-angle illumination surgical system of claim 8, wherein the first and the second optical connectors are SMA optical fiber connectors.

10. The extendable wide-angle illumination surgical system of claim 1, wherein the optical cable and the optical fiber are of equal gauge.

11. The extendable wide-angle illumination surgical system of claim 1, wherein the optical cable comprises a plurality of optical fibers.

12. The extendable wide-angle illumination surgical system of claim 1, wherein the optical fiber and the optical element are of equal gauge.

13. The extendable wide-angle illumination surgical system of claim 1, wherein the optical fiber is operably coupled to the handpiece to enable linear displacement of the optical fiber within the cannula.

14. The extendable wide-angle illumination surgical system of claim 1, further comprising a means for adjusting the length of the cannula extending from the handpiece.

15. The extendable wide-angle illumination surgical system of claim 14, wherein the means for adjusting comprises a piston, operably coupled to the cannula, operable to extend or retract the cannula from or into the handpiece.

16. The extendable wide-angle illumination surgical system of claim 14, wherein the means for adjusting further comprises a knob, operable to be moved by a user to control movement of the adjusting means.

17. The extendable wide-angle illumination surgical system of claim 14, wherein the means for adjusting further comprises a ratcheting mechanism operable to maintain a desired position of the cannula.

18. The extendable wide-angle illumination surgical system of claim 1, wherein the cannula's effective stiffness varies with the length of the cannula extending from the handpiece.

19. The extendable wide-angle illumination surgical system of claim 1, wherein the light beam comprises a beam of relatively incoherent light.

20. The extendable wide-angle illumination surgical system of claim 1, wherein the light source is a xenon light source.

21. An extendable wide-angle illuminator comprising:
an optical fiber, operable to be optically coupled to a light source and receive a light beam from the light source and transmit the light beam to illuminate an area;
a handpiece, operably coupled to the optical fiber; and
a cannula, operably coupled to the handpiece, for housing and directing the optical fiber, wherein the cannula is operable to extend and retract from the handpiece to vary a length of the cannula extending from the handpiece;
wherein the optical fiber is operably coupled to the cannula such that a distal end of the optical fiber and a distal end of the cannula remain co-incident as the length of the cannula extending from the handpiece is varied.

22. The extendable wide-angle illuminator of claim 21, further comprising an optical element, optically coupled to a distal end of the optical fiber, for receiving the light beam and scattering the light beam to illuminate the area.

23. The extendable wide-angle illuminator of claim 21, wherein the optical element comprises a small-gauge diffusive optical element.

24. The extendable wide-angle illuminator of claim 23, wherein the optical element is operably coupled to the cannula such that a distal end of the optical element and a distal end of the cannula remain co-incident as the length of the cannula extending from the handpiece is varied.

25. The extendable wide-angle illuminator of claim 21, wherein the optical fiber is a 19, 20 or 25 gauge optical fiber.

26. The extendable wide-angle illuminator of claim 21, wherein the cannula, optical fiber and the handpiece are fabricated from biocompatible materials.

27. The extendable wide-angle illuminator of claim 21, wherein the optical fiber and the optical element are of equal gauge.

28. The extendable wide-angle illuminator of claim 21, wherein the optical fiber is operably coupled to the handpiece to enable linear displacement of the optical fiber within the cannula.

29. The extendable wide-angle illuminator of claim 21, further comprising a means for adjusting the length of the cannula extending from the handpiece.

30. The extendable wide-angle illuminator of claim 29, wherein the means for adjusting comprises a piston, operably coupled to the cannula, operable to extend or retract the cannula from or into the handpiece.

31. The extendable wide-angle illuminator of claim 29, wherein the means for adjusting further comprises a knob, operable to be moved by a user to control movement of the adjusting means.

32. The extendable wide-angle illuminator of claim 29, wherein the means for adjusting further comprises a ratcheting mechanism operable to maintain a desired position of the cannula.

33. The extendable wide-angle illuminator of claim 21, wherein the cannula's effective stiffness varies with the length of the cannula extending from the handpiece.

34. The extendable wide-angle illuminator of claim 21, wherein the light beam comprises a beam of relatively incoherent light.

35. The extendable wide-angle illuminator of claim 21, wherein the light source is a xenon light source.

* * * * *